(12) United States Patent
McArthur et al.

(10) Patent No.: US 6,575,298 B1
(45) Date of Patent: Jun. 10, 2003

(54) SURGICAL INSTRUMENT HOLDER

(76) Inventors: Richard A. McArthur, 79 Swanston Street, Geelong, Victoria (AU), 3220; Robert Cockayne, 32 Saint James Street, Saint Albans Park, Victoria (AU), 3219

( * ) Notice: Subject to any disclaimer, the term of this patent is extended or adjusted under 35 U.S.C. 154(b) by 0 days.

(21) Appl. No.: 09/762,771
(22) PCT Filed: Jun. 30, 1999
(86) PCT No.: PCT/AU99/00526
§ 371 (c)(1), (2), (4) Date: Feb. 13, 2001
(87) PCT Pub. No.: WO00/09029
PCT Pub. Date: Feb. 24, 2000

(30) Foreign Application Priority Data

Aug. 14, 1998 (AU) .................................. PP5265

(51) Int. Cl.⁷ .................................. B65D 83/10
(52) U.S. Cl. ...................... 206/363; 206/806
(58) Field of Search ................. 206/363, 364, 206/365, 366, 372, 373, 219, 806; 221/96, 123, 124, 281, 303, 306; 222/158, 129, 132, 192, 143; 211/85.13, 60.1

(56) References Cited

U.S. PATENT DOCUMENTS

| | | | | | |
|---|---|---|---|---|---|
| 2,613,853 A | * | 10/1952 | Halvorsen | ................... | 222/103 |
| 2,781,152 A | * | 2/1957 | Van Slyke | ................... | 222/81 |
| 2,971,678 A | * | 2/1961 | Cazeneuve | ................... | 222/131 |
| 3,955,715 A | * | 5/1976 | Topor | ........................ | 222/143 |
| 4,039,104 A | * | 8/1977 | Mijares, Jr. et al. | ..... | 222/144.5 |
| D288,483 S | * | 2/1987 | Mora | ........................ | D24/230 |
| 4,874,113 A | * | 10/1989 | Schmidt | ...................... | 222/143 |
| 4,998,647 A | * | 3/1991 | Sharp | ......................... | 222/143 |
| 5,020,665 A | | 6/1991 | Bruno | | |
| 5,161,970 A | | 11/1992 | Baskas | | |
| 5,277,332 A | * | 1/1994 | Rogers | ........................ | 221/96 |
| 5,337,894 A | | 8/1994 | Ivey | | |
| 5,533,618 A | | 7/1996 | Pickels, Jr. | | |
| D377,593 S | * | 1/1997 | Telfer et al. | .................... | D8/71 |
| 5,871,106 A | * | 2/1999 | Oksa et al. | ................ | 211/70.6 |
| 6,269,960 B1 | * | 8/2001 | Harp | ......................... | 211/69.5 |
| 6,308,860 B2 | * | 10/2001 | Eagle | ......................... | 221/131 |
| 6,405,882 B1 | * | 6/2002 | Baxter | ..................... | 211/85.18 |

FOREIGN PATENT DOCUMENTS

| | | |
|---|---|---|
| WO | WO9307825 | 4/1993 |
| WO | WO9639091 | 12/1996 |

* cited by examiner

Primary Examiner—Shian Luong
(74) Attorney, Agent, or Firm—Flanagan & Flanagan; John R. Flanagan

(57) ABSTRACT

A surgical instrument holder for use in surgery having a holder body (10) able to hold one of a plurality of surgical instruments used together in surgery, such as a diathermy pencil and a separate suction means or two laproscopic instruments or the like, but allow easy removal of the surgical instruments. A holder attachment means (41) supports the holder body (10) and connects adjacent elongated cylinders (11, 13) at or near respective circumferential points on the elongated cylinders (11, 13) along an intersecting line between respective axes of the adjacent elongated cylinders (11, 13). A connection part (48) associated with the holder attachment means (41) enables the surgical instrument holder (10) to be removably mounted on or near a patient so that the surgical instrument holder (10) provides simultaneous access to each of the adjacent elongated cylinders (11, 13) allowing easy removal of the surgical instruments.

9 Claims, 2 Drawing Sheets

SURGICAL INSTRUMENT HOLDER

TECHNICAL FIELD

This invention relates to a surgical instrument holder able to hold a plurality of surgical instruments used together in surgery, such as a diathermy pencil and a suction instrument or laproscopic instruments or the like, and able to be removably mounted on or near a patient during surgery.

BACKGROUND ART

A quiver or scabbard comprising an open ended elongated container has been known to be used in surgery for a number of years to hold a plurality of surgical instruments such as a diathermy pencil and suction instrument for use in surgical procedures such as cauterising procedures or laproscopic instruments or the like. Many surgical techniques now require these types of instruments each having a specialised shape, size and length for the specialised surgical application.

Usually a plurality of instruments, including an electrically connected diathermy pencil and a metal tubular suction instrument, are included in the same quiver or scabbard. Clearly this is not a safe practice due to the risk of electrical mishap and possible resultant burns to the patient. Also the holding, insertion and reinsertion of a plurality of delicate expensive instruments together in a scabbard increase the likelihood of damage, and increases the risk of cross contamination of instruments during a surgical procedure.

Another development in the understanding of safe operating procedures is the understanding that live virus can be included in the resultant plume from the use of diathermy pencils or the like and this live virus can be inhaled by the surgeon. Of particular concern is the transfer of Hepatitis C from the patient by this method. One proposed solution to this problem is to include suction means integrally with the diathermy pencil to enable simultaneous plume evacuation during the surgical use of the diathermy pencil. Apart from the substantial increase in size of such a compound instrument, it is still often necessary to include a separate suction instrument for removal of other surgical waste or use in combination with other surgical instruments. Using a plurality of quivers or scabbards located in different positions provides difficulty in locating instruments used together and provides difficulty in removing instruments used together while ensuring correct handling.

DISCLOSURE OF INVENTION

It is an object of this invention to provide a surgical instrument holder that overcomes or at least ameliorates the problems of the prior art but allows ready access to a plurality of instruments for surgical procedures.

In accordance with the invention there is provided a surgical instrument holder for use in a surgery including a holder body having a plurality of discrete elongated chambers each having one closed end and one open end and each sized to hold one of a plurality of surgical instruments used together in surgery, such as a diathermy pencil and a separate suction means or two laproscopic instruments or the like, but allow easy removal of the surgical instruments, and a holder attachment means connected to the holder body and supporting the holder body and enabling the surgical instrument holder to be removably mounted on or near a patient to provide substantially adjacent access to each of the discrete elongated chambers simultaneously allowing easy removal of the surgical instruments.

In a particularly preferred form of the invention there is provided a surgical instrument holder for use in surgery having a holder body formed by a plurality of coextending elongated cylinders each having an open end at a common end of the holder body and each sized to be able to hold one of a plurality of surgical instruments used together in surgery, such as a diathermy pencil and a separate suction means or two laproscopic instruments or the like, but allow easy removal of the surgical instruments, a holder attachment means supporting the holder body and connected to adjacent elongated cylinders at or near respective circumferential points on the elongated cylinders along an intersecting line between respective axes of the adjacent elongated cylinders, and a connection part associated with the holder attachment means and enabling the surgical instrument holder to be removably mounted on or near a patient, wherein the surgical instrument holder provides simultaneously access to each of the adjacent elongated cylinders allowing easy removal of the surgical instruments.

The surgical instrument holder may be formed from a thermostable plastic or other dielectric and chemically resistant material able to insulate the surgical instruments when held separately in said discrete elongated chambers and to allow ready cleaning by autoclave or chemical means.

Preferably the holder attachment means and the holder body are shaped, attached and sized and without concave surfaces to eliminate substantially, blood and surgical residue collection points. Further, to assist the cleaning capabilities, the surgical instrument holder can have removable end caps that form respective closed ends of the discrete elongated chambers. The removable end caps can be connected to the discrete elongated chambers by screw means interfitting with external thread on the discrete elongated chambers.

BRIEF DESCRIPTION OF INVENTION

In order that the invention is more readily understood an embodiment thereof will now be described by way of example wherein.

BEST MODE FOR CARRYING OUT THE INVENTION

Figure 1:
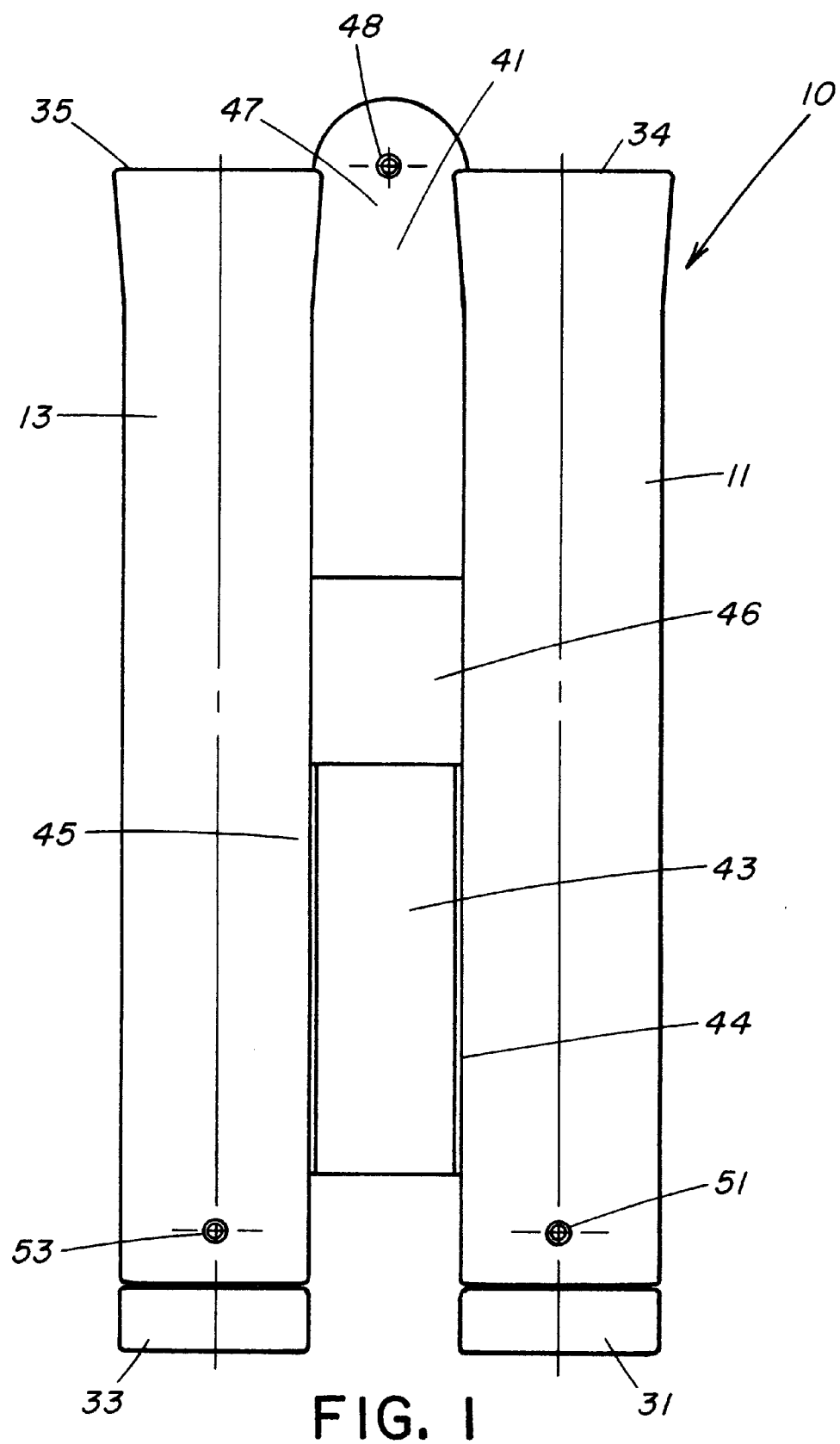
FIG. 1 is a rear plan view of a surgical instrument holder according to a first embodiment of the invention.
Figure 2:
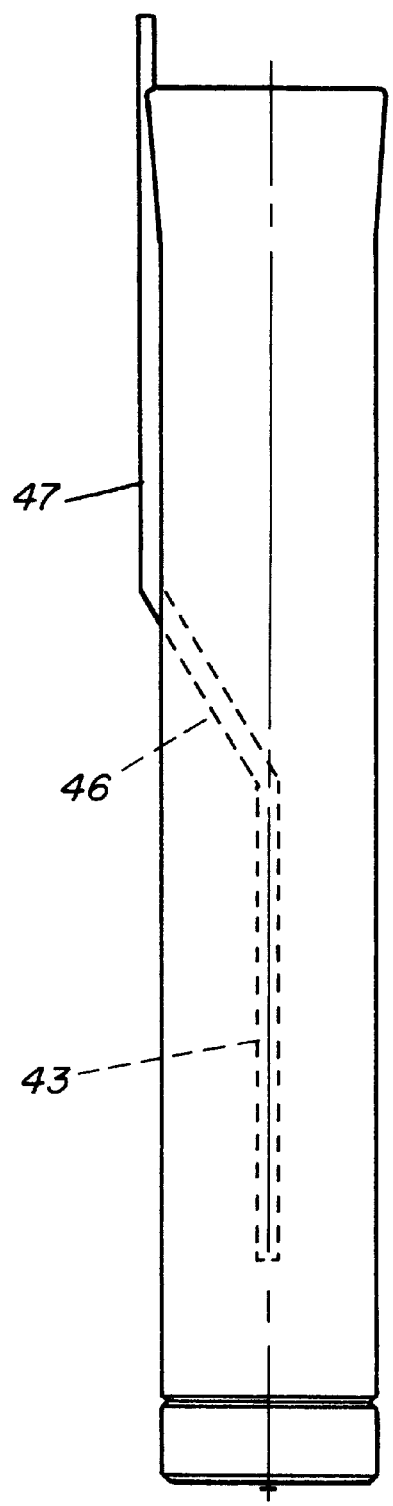
FIG. 2 is a side diagrammatic side view of the surgical instrument holder of FIG. 1.

Referring to the drawings there is shown a surgical instrument holder including a holder body 10 having a plurality of discrete elongated chambers in the form of coextending elongated cylinders 11, 13 each having one closed end 31, 33 and one open end 34, 35 and each sized to hold one of a plurality of surgical instruments used together in surgery such as a diathermy pencil and a suction means or laproscopic instruments or the like. The respective chambers are formed by the continuous curved internal surfaces of the elongated cylinders 11, 13. The elongated cylinders 11, 13 have continuous curved external surfaces encompassing and spaced outwardly from the continuous curved internal surfaces. The elongated cylinders 11, 13 are the same diameter and length and are aligned to be fully co-extensive so that the open ends 34, 35 align. A holder attachment means 41 is connected to portions of the continuous curved external surfaces of the coextending elongated cylinders 11, 13 to retain them in relative position and to support the holder body 10 enabling the surgical instrument holder to be removably mounted on or near a patient to provide substantially adjacent access to each of the discrete elongated chambers simultaneously allowing easy removal of the surgical instruments.

The body of the surgical instrument holder 10 of another preferred embodiment has two aligned different length cylinders each having a closure at a common end and an opening at the opposite common end. This structure enables a diathermy pencil to be held in the larger cylinder and a suction instrument to be held in the smaller cylinder with the open ends aligned.

In the surgical instrument holder 10 shown in the drawings the attachment means 41 is formed as a bent elongated flat strip having constant width with a first planar portion 43 extending between the lines of the closest radial points of the adjacent aligned cylinders 11, 13. The outer parallel edges 44, 45 of the first planar portion 43 are plastic butt welded to respective outer surface of the cylinders 11, 13 along the longitudinally extending lines of closest radial points. The shaped attachment means 41 extends via an angled part 46 to a second planar portion 47 parallel to the first planar portion 43. The second planar portion 47 extends substantially along a tangential plane to both of the adjacent aligned cylinders 11, 13 a quarter revolution around each cylinder from the plastic weld join 44, 45. This provides planar aligned surfaces of the cylinders 11, 13 and shaped attachment means 41 to allow for flat placement of the surgical instrument holder 10 on patient surgical drapes covering a patient during surgery or nearby. The end of the second planar portion 47 of the attachment means 41 not connected to the cylinders 11, 13 is able to be attached by connection means to surgical drapes or the like by surgical clips mounted on a ring inserted in a hole 48 in the end of the attachment means 41.

The upper openings 34, 35 of the cylinders 11, 13 have outwardly extending flanges to allow easy insertion and removal of the surgical instruments. At the other end of the cylinders 11, 13 near the base is an outlet hole 51, 53 which allows for drainage of liquids from the instruments such as excess blood. These outlet holes 51,53 also act as pressure relief ports to allow the surgical instrument holder 10 to be autoclaved or otherwise pressure steam cleaned without a build up of pressure in the tubular enclosure.

The end of the holder 10 also incorporates a screw threaded end caps 31, 33 engaging with respective screw thread on the outer side of the cylinders 11, 13 to provide a smooth continuous inner cylindrical surface and allowing the end caps 31, 33 to be easily connected. The lack of internal connection surfaces results in a smooth continuous surface for thorough mechanical or other cleaning of the surgical instrument holder 10. The removal aspect of the end caps 31, 33 further improves the cleaning capabilities of this surgical instrument holder 10. Still further, the minimisation of external concave shapes also improves the cleaning capabilities of the surgical instrument holder 10. In surgery these cleaning capabilities are of significant importance to the usability and reusability of surgical items.

The closed bottom end of the plurality of cylinders 11,13 may be by a removable cap that is clipped on. The optimal cap is a screw cap that is attached to an external thread on the outer bottom of the cylinders. This strong structure is not deformed by a plurality of autoclaving procedures required for constantly used products in hospital surgeries. The cap however could comprise a single clip on piece to close both bottom ends of the cylinders to minimise the number of pieces while still allowing easy cleaning. The attachment of the single piece may be by clips attaching to outer parts of the surgical instrument holder body.

The cylinders 11, 13 preferably have a length of about 15 to 35 centimeters and with a cylindrical internal diameter of between 35 to 50 millimeters. These cylinders can be other lengths and diameters dependent on the surgical instrument to be held.

In construction of the surgical instrument holder body 10 the coextending elongated cylinders 11, 13 and the attachment means 41 can be formed integrally such as by injection moulding or the like, or made in separate parts which are attached at radial portions of the cylinders 11, 13. However the construction must minimise points of collection of blood or surgical waste. The join at the side of the cylinders 11, 13 at the closest radial points of the cylinders that is along the plane comprising the axis of both cylinders 11, 13 provides the best joining angle and the least width of the attachment means 41.

The material of the surgical instrument holder 10 is a thermostable plastic able to withstand multiple autoclaving procedures as is required for sterilising and cleaning surgical instruments and associated material in hospitals. The material is also a dielectric and chemically resistant material able to insulate electrically the surgical instruments when held separately in said coextending elongated cylinders 11, 13.

The above description of the preferred embodiments of the invention is provided as illustrative only of the invention and not limiting.

What is claimed is:

1. A surgical instrument holder for use in a surgery, comprising:

a holder body (10) having a plurality of discrete elongated chambers (11), (13) each having one closed end (31), (33) and one open end (34), (35) and each sized to hold one of a plurality of surgical instruments used together in surgery, but allow easy removal of the surgical instruments;

removable end caps (31), (33) removably attached on the holder body so as to form the respective closed ends of the discrete elongated chambers (11), (13) and, upon removal of the end caps, enable thorough cleaning of the discrete elongated chambers (11), (13); and a holder attachment means (41) connected to the holder body (10) and supporting the holder body (10) and enabling the surgical instrument holder to be removably mounted adjacent a patient to provide substantially adjacent access to each of the discrete elongated chambers (11), (13) simultaneously allowing easy removal of the surgical instruments.

2. A surgical instrument holder according to claim 1 wherein the holder body and holder attachment means are formed from a thermostable plastic being a dielectric and chemically resistant material able to insulate the surgical instruments from each other when held separately in said discrete elongated chambers (11), (13) and to allow ready cleaning.

3. A surgical instrument holder according to claim 1 wherein the removable end caps (31), (33) forming respective closed ends of the discrete elongated chambers (11), (13) are connected to the discrete elongated chambers (11), (13) by screw means interfitting with respective external thread on the discrete elongated chambers (11), (13).

4. A surgical instrument holder for use in a surgery, comprising:

a holder body (10) formed by a plurality of coextending elongated cylinders (11), (13) disposed adjacent one another, each of the elongated cylinders having a longitudinal axis and an open end (34), (35) at a common end of the holder body (10) and each of the elongated cylinders sized to be able to hold one of a plurality of surgical instruments used together in surgery, but allow easy removal of the surgical instruments;

a holder attachment means (41) supporting the holder body (10) and having a first portion connected to the adjacent elongated cylinders (11), (13) at respective circumferential points on the elongated cylinders (11), (13) along a plane extending between respective longitudinal axes of the adjacent elongated cylinders (11), (13) and a second portion extending between the adjacent elongated cylinders (11), (13) along a plane connecting tangential points of outer parts of the adjacent elongated cylinders (11), (13) so as to provide a substantially planar lower resting surface of the surgical instrument holder allowing for flat positioning on a surgical drape around a patient; and a connection part (48) extending from the second portion of the holder attachment means (41) and enabling the surgical instrument holder to be removably mounted adjacent a patient so as to provide simultaneous access to each of the adjacent elongated cylinders (11), (13) of the holder body allowing easy removal of the surgical instruments.

5. A surgical instrument holder according to claim 4 wherein the elongated cylinders (11), (13) have fluted open ends (34), (35).

6. A surgical instrument holder according to claim 4 wherein the holder body and holder attachment means are formed from a thermostable plastic being a dielectric and chemically resistant material able to insulate the surgical instruments from each other when held separately in said coextending elongated cylinders (11), (13) and to allow ready cleaning.

7. A surgical instrument holder according to claim 4, further comprising:

removable screw threaded end caps (31), (33) removably attached on the discrete elongated cylinders (11), (13) of the holder body (10) so as to form the respective closed ends of the discrete elongated cylinders (11), (13) and, upon removal of the end caps (31), (33), enabling thorough cleaning of the discrete elongated cylinders (11), (13).

8. A surgical instrument holder for use in a surgery, comprising:

a holder body (10) formed by a plurality of coextending elongated cylinders (11), (13) disposed adjacent one another, each of the elongated cylinders having a longitudinal axis and an open end (34), (35) at a common end of the holder body (10) and each of the elongated cylinders sized to be able to hold one of a plurality of surgical instruments used together in surgery, but allow easy removal of the surgical instruments;

removable end caps (31), (33) removably attached on the coextending elongated cylinders so as to form respective closed ends of the coextending elongated cylinders (11), (13); and a holder attachment means (41) supporting the holder body (10) and connected to the adjacent elongated cylinders (11), (13) at respective circumferential points on the elongated cylinders (11), (13) along a plane extending between respective longitudinal axes of the adjacent elongated cylinders (11), (13); and a connection part (48) extending from the holder attachment means (41) and enabling the surgical instrument holder to be removably mounted adjacent a patient so as to provide simultaneous access to each of the adjacent elongated cylinders (11), (13) of the holder body allowing easy removal of the surgical instruments.

9. A surgical instrument holder according to claim 8 wherein the removable end caps (31), (33) forming respective closed ends of the coextending elongated cylinders (11), (13) are connected to the coextending elongated cylinders (11), (13) by screw means interfitting with external thread on the coextending elongated cylinders (11), (13).

* * * * *